(12) United States Patent
Carter et al.

(10) Patent No.: US 7,153,263 B2
(45) Date of Patent: *Dec. 26, 2006

(54) WIRELESS LAN ARCHITECTURE FOR INTEGRATED TIME-CRITICAL AND NON-TIME-CRITICAL SERVICES WITHIN MEDICAL FACILITIES

(75) Inventors: Scott J. Carter, Seal Beach, CA (US); Edward L. Flanders, Coto de Caza, CA (US); Stephen E. Hannah, Placentia, CA (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 296 days.

This patent is subject to a terminal disclaimer.

(21) Appl. No.: 10/795,477

(22) Filed: Mar. 8, 2004

(65) Prior Publication Data

US 2004/0170154 A1 Sep. 2, 2004

(51) Int. Cl.
*A61B 5/00* (2006.01)
(52) U.S. Cl. ............... 600/300; 128/920; 128/903
(58) Field of Classification Search ........ 600/300–301; 128/903–905, 920
See application file for complete search history.

(56) References Cited

U.S. PATENT DOCUMENTS 6,406,426 B1* 6/2002 Reuss et al. ............... 600/300
6,440,068 B1* 8/2002 Brown et al. ............... 600/300
6,659,947 B1* 12/2003 Carter et al. ............... 600/300

OTHER PUBLICATIONS

Chris Anderson, The WI-FI Revolution, Wired, 2003, pp. 6-16.

* cited by examiner

*Primary Examiner*—Max F. Kindenburg
*Assistant Examiner*—Michael C Astorino
(74) *Attorney, Agent, or Firm*—Andrus, Sceales, Starke & Sawall, LLP (57) ABSTRACT

A wireless local area network (WLAN) system comprises multiple access points that are distributed throughout a medical facility to provide wireless access to a hardwired network. The access points implement multiple WLAN protocols, including a realtime protocol for realtime patient monitoring (telemetry) and a standard WLAN protocol (such as IEEE 802.11 within an ISM band) for providing general-purpose wireless access. Some or all of the access points preferably implement both WLAN protocols such that the different WLANs and wireless device types share network access resources. Some or all of the access points may also include RF location-tracking modules which may be used to track locations of patients, hospital personnel, capital equipment, and/or disposable medical supplies. Also disclosed are an antenna design which may be used with the access points to improve reception (particularly for patient monitoring), and a TDMA timeslot rotation method for avoiding lockstep interference between access points that operate on the same channel.

7 Claims, 5 Drawing Sheets

WIRELESS LAN ARCHITECTURE FOR INTEGRATED TIME-CRITICAL AND NON-TIME-CRITICAL SERVICES WITHIN MEDICAL FACILITIES

RELATED APPLICATIONS

This application claims priority to U.S. application Ser. No. 10/640,784, filed on Aug. 14, 2003, which claims priority to U.S. application Ser. No. 09/615,362, filed on Jul. 13, 2000, now U.S. Pat. No. 6,659,947 issued on Dec. 9, 2003.

BACKGROUND OF THE INVENTION

1. Field of the Invention

The present invention relates to computer networks for realtime and non-real-time applications within medical facilities.

2. Description of the Related Art

Many hospitals today are equipped with a hospital information system (HIS) for handling billing, administration, and other business-related matters. Hospitals are also commonly equipped with clinical information systems (CIS) for storing and managing the clinical data of patients. Both types of systems typically operate over a hardwired infrastructure, such as a local area network (LAN).

Hospitals also commonly include special telemetry systems for monitoring the realtime ECG and other physiologic data of patients. Typically, these systems include special wireless transmitters that attach to respective patients, or to the bedside monitors for such patients. Each wireless transmitter transmits the physiologic data of a patient over a wireless channel to a receiving node, which in turn makes the data available for realtime monitoring and viewing on a hardwired monitoring network.

Because of the special requirements associated with handling realtime telemetry data and supporting patient mobility, the hardwired networks used for patient monitoring are normally separate from the networks used for HIS and CIS applications. As a result, the medical facility typically must set up and support two separate computer networks and separate RF networks. Further, existing systems generally do not support wireless access to the HIS, CIS, and other information systems of the hospital LAN.

The present invention seeks to reduce or eliminate these deficiencies while providing new types of wireless applications and services to network users. The invention also provides novel hardware and methods for improving the reliability of wireless LANs.

SUMMARY OF THE INVENTION

The present invention provides a wireless local area network (WLAN) system: which comprises multiple access points that are distributed throughout a medical facility to provide wireless access to a hardwired network. The access points implement multiple WLAN protocols, including a realtime protocol for realtime patient monitoring (telemetry) and a standard WLAN protocol (such as IEEE 802.11 within an ISM band) for providing general-purpose wireless access. The system thereby allows a single hardwired network to be used for realtime patient monitoring, while providing general-purpose wireless access to resources on the hardwired network such as HIS and CIS databases. Some or all of the access points preferably implement both WLAN protocols such that the different WLANs and wireless device types share network access resources.

In accordance with one aspect of the invention, some or all of the access points may also include RF location-tracking modules that receive signals from patient transceivers and/or other types of location tracking devices. Application software running on the hardwired network uses these devices to track the locations of patients, hospital personnel, capital equipment, and/or disposable medical supplies. The location data may be stored on the hardwired network by a location-tracking server which makes the data available for near-realtime viewing. The location data may also be used for a variety of other applications, including patient-flow analysis and inventory tracking of disposable equipment.

The present invention also provides an antenna design which may be used with 25 the access points to improve reception (particularly for patient monitoring), and provides a TDMA timeslot rotation method for avoiding lockstep interference between access points that operate on the same channel. In addition, the invention provides various applications for which the system may be used, including bedside entry of patient data and prescriptions using wireless writing tablets, the use of wireless barcode scanners to read-in patient ID data from physical charts, and a two-way paging system in which a PDA device may be used to receive alert messages and view corresponding patient data.

BRIEF DESCRIPTION OF THE DRAWINGS

The invention will now be described with reference to the following drawings of illustrative embodiments of the invention.

Reference numbers are re-used throughout the drawings to indicate a correspondence between components.

DETAILED DESCRIPTION OF THE PREFERRED EMBODIMENTS

The specific embodiments shown in the drawings and described herein are intended to illustrate, and not limit, the scope of the invention. The scope of the invention is defined by the appended claims.

Throughout the description, the terms "time-critical" and "realtime" will be used generally to refer to applications and data transfer methods in which data is transferred with a known, maximum latency. Such applications include, for example, realtime monitoring of patient ECG waveforms.

The present invention is related generally to wireless telemetry systems of the type described in U.S. Pat. No. 5,944,659, assigned to VitalCom Inc. ("the '659 patent"), the disclosure of which is hereby incorporated by reference. In such a system, network access points (referred to as VCELLs in the '659 patent) are positioned throughout a medical facility to provide overlapping zones or cells of data reception coverage. These access points, which are connected to a hardwired computer network, communicate bi-directionally with wireless remote patient transceivers (also referred to as "telemeters") that attach to individual patients or to bedside instruments for such patients. The access points and patient transceivers communicate using a TDMA (time division multiple access) protocol in which timeslots are assigned by the access points to the patient transceivers. Nearby access points operate on different channels (e.g., using different hop sets or using different fixed frequencies) to avoid interference.

In operation, each patient transceiver transmits physiologic data of a respective patient in real time to the hardwired network via an access point (or possibly to multiple access points concurrently). The realtime physiologic patient data is in turn monitored by a human operator and/or automated monitoring software using computers connected to the hardwired network. To maintain connectivity to the hardwired network, each patient transceiver dynamically monitors the wireless link conditions offered by nearby access points. Based on assessments of these link conditions and timeslot availability conditions, the remote telemeters dynamically select the access points with which to establish or discontinue data connections. Thus, as a patient moves throughout the medical facility, the patient's transceiver automatically connects to, and disconnects from, specific access points as needed to maintain connectivity to the hardwired network.

The present invention extends the capabilities of the above-described architecture such that the wireless telemetry infrastructure may additionally be used for non-time-critical applications such as patient/object location tracking, paging and general-purpose network access. This is accomplished by allocating one set of wireless channels to time-critical data transmissions and another set of wireless channels to non-time-critical applications. The time-critical and non-time-critical channels may, but need not, fall within separate frequency bands. The time-critical and non-time-critical wireless transmissions are preferably handled by separate access point transceivers, so that data transmissions may be prioritized for routing on the hardwired network based on the type of access point transceiver used. Both types of transceivers (time-critical and non-time-critical) may be incorporated into a common, "multi-purpose" access point to reduce the total number of access points needed within a given installation.

The architecture allows a diverse set of wireless devices to share a common wireless infrastructure. These devices may include, for example realtime telemetry devices (patient transceivers), personal digital assistants (PDAs), laptop computers, object location-tracking devices, pagers, voice-over-1P portable phones, tablet type devices, and wireless barcode scanners. The invention may be used, for example, to supplement a preexisting hardwired hospital network with wireless networking and patient monitoring capabilities. The invention may also be embodied within a complete system that serves all of the medical facility's wireless and hardwired networking needs.

I. System Overview

Figure 1:
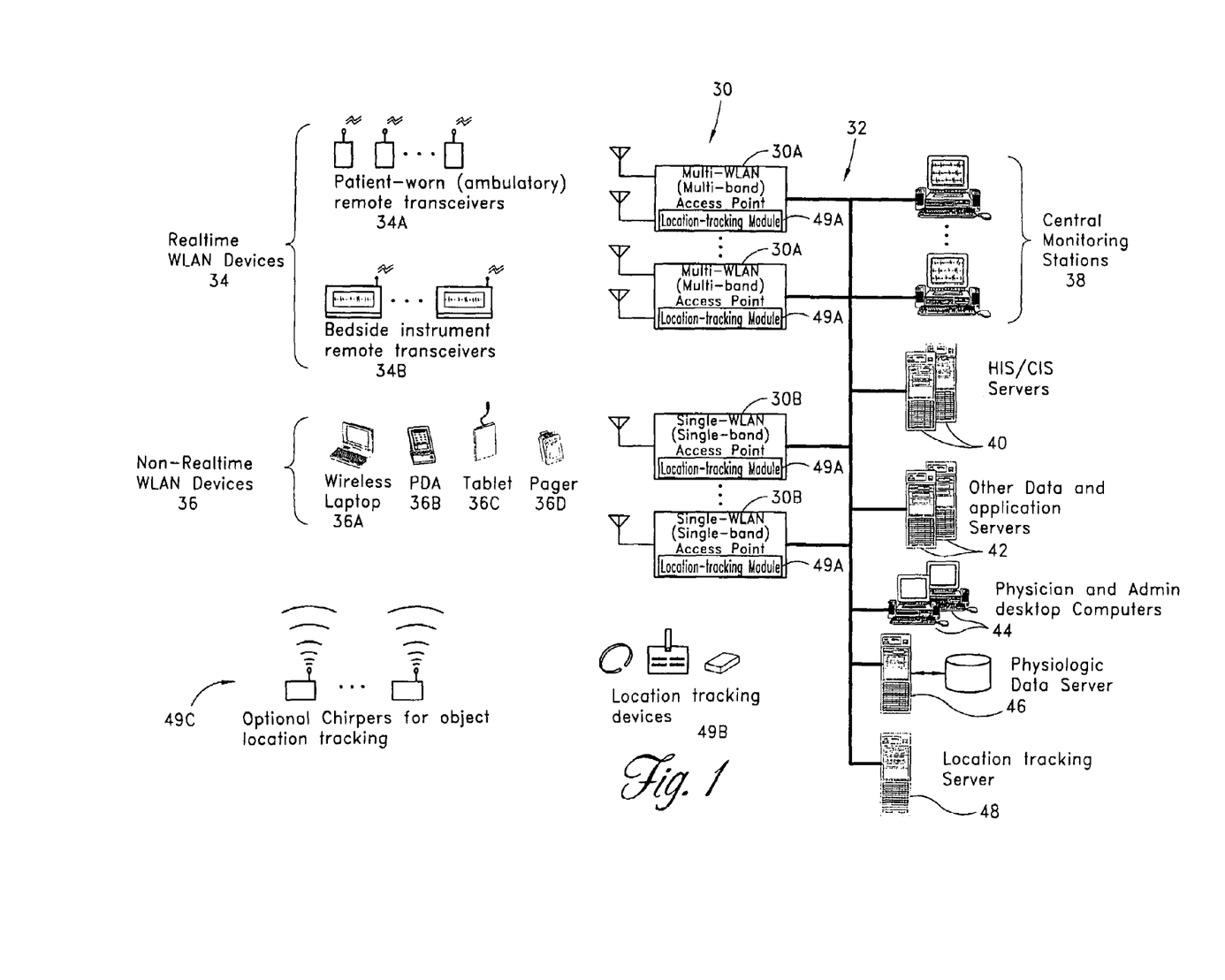
FIG. 1 illustrates the architecture of an example system constructed in accordance with the invention.

FIG. 1 illustrates a system according to one embodiment of the invention. The system includes multiple access points 30 that are interconnected by a hardwired hospital network 32. The access points 30 provide connectivity between the hospital network 32 and various types of wireless devices, including remote patient transceivers 34 used for realtime patient monitoring, and various type of devices 36 used for non-time-critical applications. The access points 30 are spatially distributed throughout the medical facility to provide zones or "cells" of coverage. The access points 30 communicate bi-directionally with the wireless devices 34, 36 using one or more wireless LAN (WLAN) protocols that support the mobility of devices from cell to cell. As described below, a realtime WLAN protocol of the type disclosed in the '659 patent may be used to communicate with the devices 34 used for time-critical applications, while a standard wireless LAN protocol such as that of IEEE 802.11 may be used to communicate with the other devices 36.

The hardwired hospital network 32 may consist of a single, unified full duplex LAN, such as a 100BaseT Ethernet LAN, that is used both for realtime patient monitoring and for non-realtime applications (including HIS and CIS). Alternatively, the hardwired network may include two or more interconnected LANs, one of which is generally dedicated to one of the two traffic types. In the illustrated embodiment, the hardwired network 32 includes central monitoring stations 38 for viewing and monitoring realtime data of patients; servers 40, 42 for handling HIS, CIS, and other non-realtime or near realtime applications; computers 44 used by clinicians and hospital administrators to access the network; a physiologic data server 46 (for storing and providing non-realtime access to telemetry data), and a location tracking server 48. Any of a variety of other types of computer systems and associated applications may be provided on the network. Although the various severs are shown in FIG. 1 as separate computer systems for clarity, a given computer may act as the server for multiple, unrelated applications (e.g., HIS and location tracking).

In accordance with the invention, the access points 30 collectively provide wireless access to the hospital network 32 over two sets of channels, one set of which is used for time-critical transmissions ("realtime channels"), and the other of which is used for non-time-critical transmissions ("non-realtime channels"). The realtime channels support wireless data transfers to the hardwired network 32 with a known, maximum latency. These channels are preferably used for telemetry of ECG and other physiologic data from patient transceivers 34 (including both ambulatory transceivers 34A and instrument transceivers 34B) to the hardwired network 32. The realtime channels may also be used for other types of time-critical applications, such as voice communications and video streaming.

The non-realtime channels are based on an industry-standard WLAN protocol such as IEEE 802.11, and are preferably used to provide wireless access to servers 42–48 used for HIS, CIS, physiologic data retrieval, and location tracking applications. These channels may also be used to implement a paging system and to provide wireless access to other types of network resources. As depicted in FIG. 1, the types of wireless devices 36 which may use the non-realtime WLAN include, for example, laptop computers 36, PDAs 36B, tablets 36C for data entry (e.g., entry of prescriptions and clinical data), pagers 36D, and voice-over-IP portable phones. Some or all of these devices 36 may include bar code scanners (not shown) which may be used, for example, to scan-in information about a patient or a prescription. Examples of applications for which the various types of non-realtime WLAN devices 36 may be used are described below.

The access points 30 preferably provide the two types of wireless channels by implementing two separate WLANs: a realtime WLAN and a standard, non-realtime WLAN. In the preferred embodiment, the realtime WLAN operates in the Wireless Medical Telemetry Service (WMTS) 608–614 MHz band using a protocol of the type described in the '659 patent; and the non-realtime WLAN operates in the 2.4 GHz Industrial, Scientific, and Medical (ISM) band according to the IEEE 802.11 WLAN standard. As depicted in FIG. 1 and described below, some or all of the access points 30 preferably implement both WLANs, and thus serve as multi-band, multi-purpose access points 30A. The architecture thus allows different WLANs and wireless device types 34, 36 to share network access resources on the hardwired network 32.

As will be recognized, a variety of other options are possible for providing the two types of wireless channels. For example, a single WLAN standard could potentially be used to provide both types of channels (IEEE 802.11 currently does not provide guaranteed latency, and thus is not well suited for realtime data transfers, but may be modified or superceded in the future to provide realtime services.) Further, both the realtime and the non-realtime channels could share the same frequency band (e.g., the 2.4 GHz ISM band) by using spatial and angle separation, or another channel separation technique, to provide separation between channels. Further, the system could use additional or alternative WLAN specifications, such as the Bluetooth™ specification, and could use other frequency bands such as the 1395–1400 MHz and 1429–1432 MHz WMTS bands and the 900 MHz and 5.2 GHz ISM bands (and other bands made available by the FCC or other regulatory entity). Thus, it should be understood that the references to specific frequency bands, WLAN specifications, channel separation methods, etc. are provided for purposes of illustrating one preferred embodiment, and not to limit the scope of the invention.

The patient transceivers 34A, 34B, and the access point transceivers 52A (FIG. 3) with which they communicate, may be constructed and may operate as described in the '659 patent. Any of a variety of alternative transceiver designs and protocols that support the realtime transmission of data may be used. The physiologic data collected from the patient transceivers 34 is made available for realtime viewing and monitoring on the hospital network 32 via the central monitoring stations 38. This may be accomplished, for example, using protocols layered on UDP/IP multicasting, or by using other realtime network data transfer methods that are known in the art such as RS\TP (Resource Reservation Protocol) and RTP (Realtime Transport Protocol). The physiologic data may also be stored in a database of the physiologic data server 46 for subsequent retrieval. The various non-realtime WLAN devices 26 in the preferred embodiment are commercially-available devices that include off-the-shelf 802.11 wireless modems. The system may also include wireless devices that use both types of WLANs (e.g., a patient transceiver 34 which includes an 802.11 transceiver for voice communications).

The multi-WLAN access points 30A implement both WLANs (preferably in separate bands, as described above) to support for both realtime and non-realtime applications. Where the hospital network 32 consists of a single, unified LAN, the multi-WLAN access points 30A merge or multiplex the incoming wireless data streams from the different WLANs/bands onto the hardwired LAN 32, giving priority to time-critical data as needed to provide a known maximum latency. Where separate hardwired LANs are provided for time-critical versus non-time-critical applications, each multi-WLAN access point may be provided with two separate network interfaces—one for each WLAN (see FIGS. 2 and 4). The system may be designed such that that the cell footprints for the different WLANs are roughly the same size. Where footprint sizes are different, the smaller footprint may be used to determine the minimum distance by which access points are spaced apart.

Figure 2:
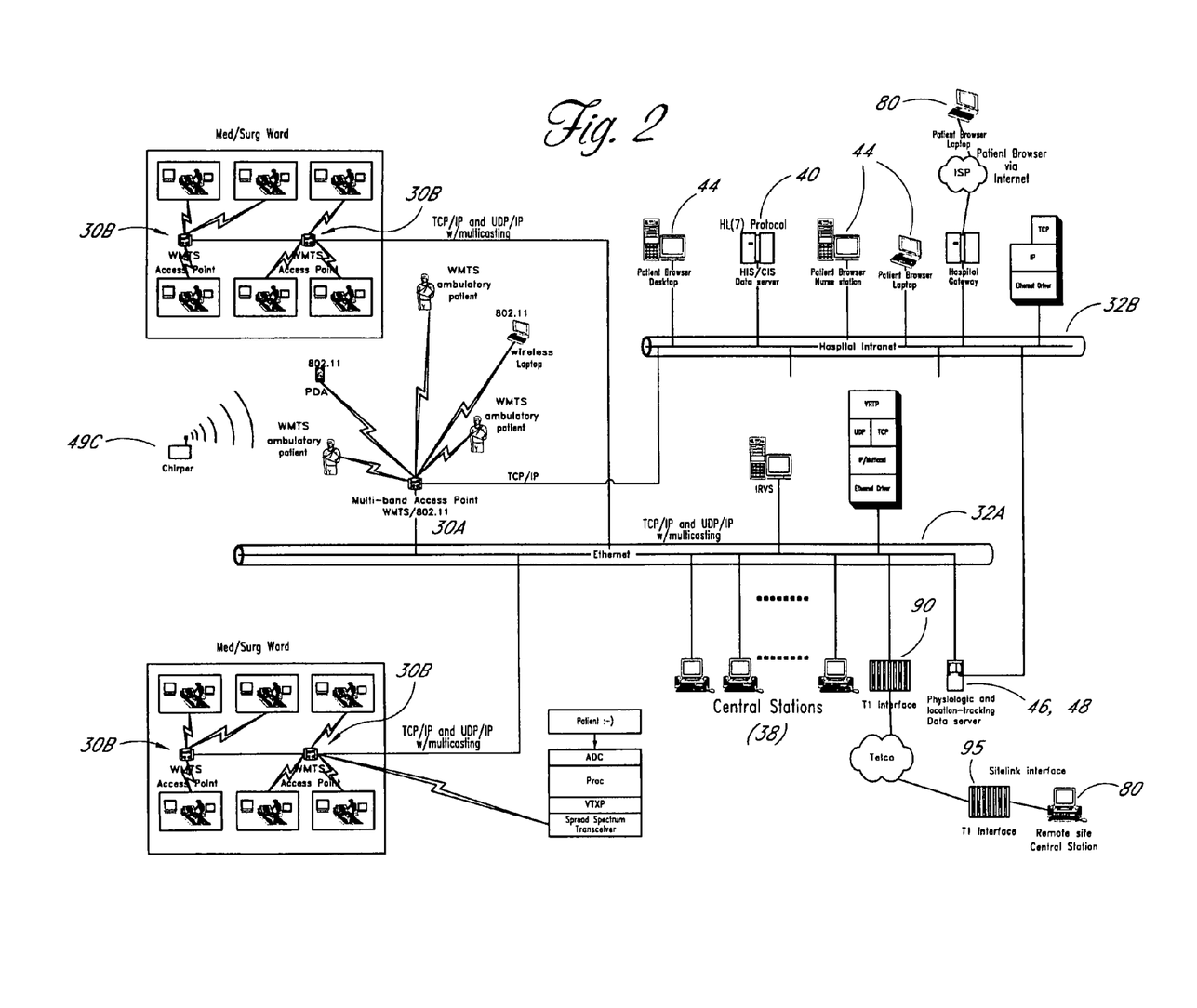
FIG. 2 illustrates a typical installation of the FIG. 1 system within a medical 10 facility.

As illustrated in FIG. 1, the system may also include single-WLAN, single-band access points 30B that implement only one of the two WLAN specifications. Each single-WLAN access point may be configured as either a realtime WLAN access point or a non-realtime WLAN access point. Single-WLAN access points may be desirable, for example, in regions of the hospital used primarily for one type of application (time-critical or non-time-critical) and not the other. For example, it may be desirable to provide several WMTS access points 30B within a step down ward or other high-volume patient area, as shown in FIG. 2.

As will be recognized by the foregoing, the system can alternatively be implemented with single-WLAN access points 30B only, wherein some of the access points implement a realtime WLAN and other access points implement a non-realtime WLAN. The use of multi-WLAN access points, however, provides the important benefit of allowing the two different categories of wireless devices 34, 36 to share network access resources, thus reducing the quantity of access point resources and the cost of the installation.

As further depicted in FIG. 1, some or all of the access points 30 preferably include location-tracking receivers 49A for tracking the locations of objects 49B within the medical facility. As illustrated, these objects 49B may include, for example, patient-worn wristbands, ID badges worn by hospital personnel, and adhesive devices that attach to capital and/or disposable equipment. Each such device may include a small, battery powered transceiver, transmitter or transponder which transmits an ID signal to the location-tracking receivers 49A. The patient transceivers 34A, 36A include similar functionality to support the location-tracking of patients.

Any of a variety of object location-tracking methods may be used within the system to track the locations of the devices 34, 49B. One such technique is described in U.S. provisional appl. No. 60/193,655, filed Mar. 31, 2000, the disclosure of which is hereby incorporated by reference. With this method, chirpers 49C are positioned throughout the regions of the medical facility in which location-tracking functionality is desired. The chirpers 49C periodically transmit unique ID signals at predetermined signal strengths. These signals are received by nearby location-tracking devices 34, 49B that are attached to the objects to be tracked. The location-tracking devices 34, 49B retransmit the ID signals they receive (preferably in an ISM band) along with a corresponding received signal strength indicator (RSSI). The retransmitted ID and RSSI data is received by nearby location-tracking modules 49A, which forward such data to a location tracking server 48. The location tracking server 48 uses the combination of chirper IDs and RSSI values it receives from a given location tracking device at a given point in time to determine the device's current location. Other location tracking methods and architectures that may be used include those described in the '659 patent and in U.S. provisional application 60/193,650, filed Mar. 31, 2000, the disclosure of which is hereby incorporated by reference. GPS-based system may also be used for this purpose. Regardless of the particular tracking method used, the near-realtime location information for the tracked objects is preferably stored by the location-30 tracking server 48 and is made available on the network 32.

FIG. 2 illustrates a typical installation of the system within a hospital. In this example, two separate Ethernet LANs 32A, 32B are provided in the hospital—one for realtime patient monitoring 32A and one for non-realtime applications 32B. This may be desired, for example, where the pre-existing hospital LAN is not adequate for realtime patient monitoring. It will be recognized, however, that the two distinct LANs in FIG. 2 could be replaced with a single LAN. In the illustrated embodiment, a physiologic data server 46 (which also servers as a location tracking server) stores the physiologic data captured by the telemetry system, and makes this data available on the non-realtime LAN 32B for near-realtime and other applications. This server 46 may be used, for example, to provide ECG snapshots or streamed ECG waveforms to an 802.11 device 36, to a local computer 40, 44, or to a remote computer 80 via the Internet. To support the local or remote viewing of streamed physiologic data via a standard Web browser program, the physiologic data server 46 and the machines 40, 44, 80 may be provided with VitalCom Inc.'s PatientBrowser™ software, which functions generally as described in U.S. Provisional Appl. No. 60/192,510, filed Mar. 28, 2000, the disclosure of which is hereby incorporated by reference.

The example system shown in FIG. 2 includes two types of access points—multi-band (WMTS/802.11) access points 30A, and single-band (WMTS) access points 30B used for patient monitoring. The WMTS access points 30B are positioned primarily in the patient areas of the hospital, such as step-down units and surgical wards as shown. Because each such access point 30B can only accommodate (maintain data connections with) a fixed number of patients at a time, multiple access points may be positioned side-by-side within high volume patient areas. The multi-bandlmulti-purpose access points 30A (one shown) may be positioned throughout the hospital in regions in which it is desired to have 802.11 access to the hospital network 32. In addition to realtime patient monitoring, these access points 30A may be used to provide wireless access to various network resources, such as HIS and CIS databases, previously-captured ECG data, the Internet, and various types of application functionality. The multi-band access points 30A may also be used to implement a paging system.

As described above, some or all of the access points 30A, 30B may include location-tracking modules 49A for tracking the locations of, e.g., patient, hospital personnel, capital equipment, and disposable supplies. If the location-tracking scheme uses chirpers 49C, the chirpers 49C (one shown) are positioned throughout the medical facility in the patient areas and other areas in which location-tracking is desired.

As depicted in FIG. 2, the system may also include T1 or other interface 95 for supporting the remote viewing of realtime telemetry data. The SiteLink system of VitalCom Inc. may be used for this purpose.

II. Access Point Architecture

Figure 3:
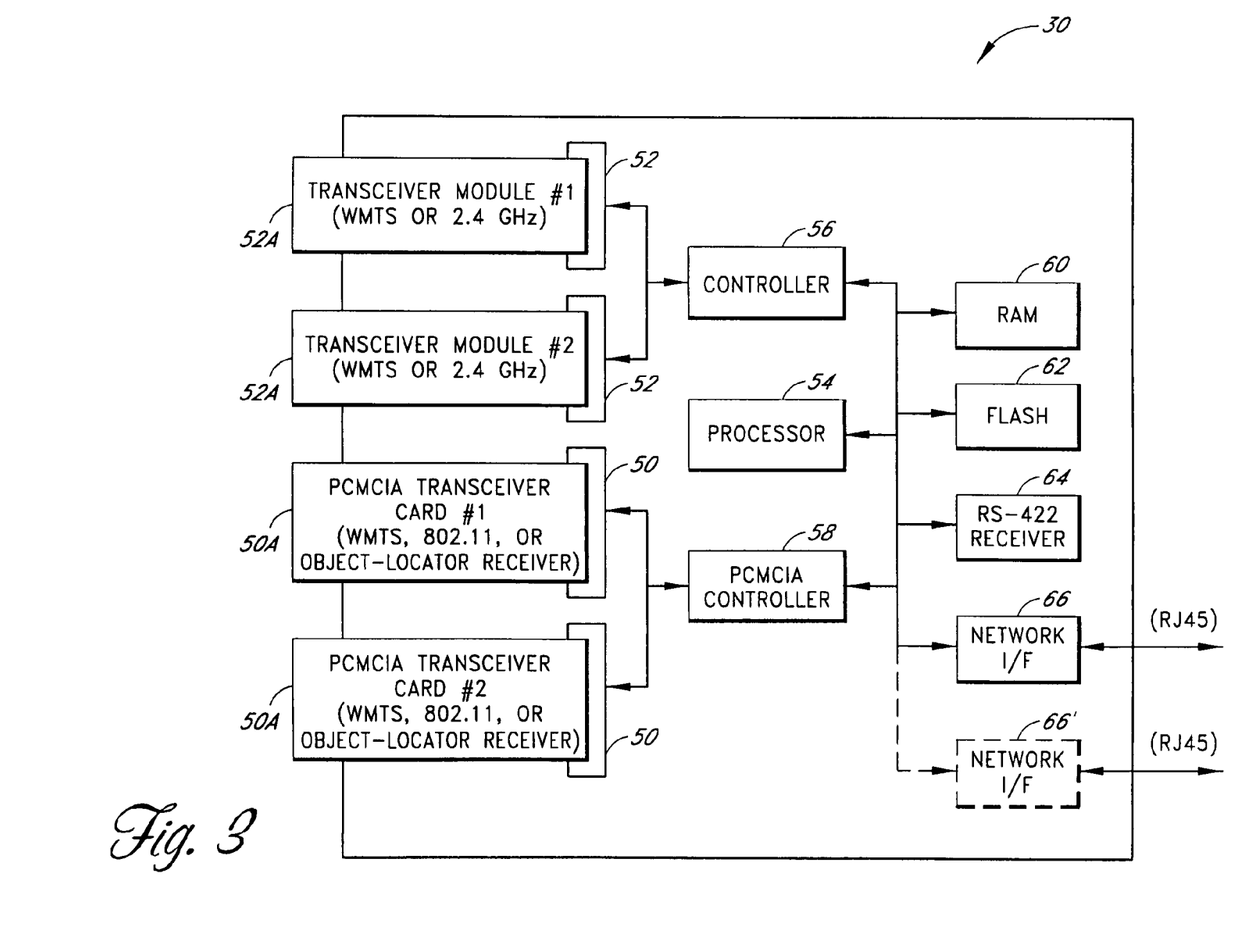
FIG. 3 illustrates an access point architecture that supports a variety of configurations.

FIG. 3 is a block diagram of a configurable access point 30 according to one embodiment of the invention. The access point includes two PCMCIA ports or slots 50 for receiving respective PCMCIA cards 50A. Each PCMCIA slot 50 may be populated with one of the following types of PCMCIA cards: a WMTS transceiver module (for time-critical applications), an off-the-shelf or custom 802.11 transceiver module (for non-time-critical applications), or an object-locator receiver module 49A. The object-locator modules are preferably non-802.11, non-WMTS devices which operate in an ISM band as set forth in U.S. Prov. Appl. No. 60/192,510, referenced above. Commercially-available location tracking modules may alternatively be used for this purpose.

The access point 30 also includes two non-PCMCIA ports or slots 52 for receiving two additional transceiver modules 52A. Each of these slots 52 uses the form factor of the commercially-available Digital Wireless Inc. WIT2410 transceiver, and may be populated with either a WMTS or a 2.4 GHz transceiver module 52A. These transceiver modules 52A are preferably adapted to be used for telemetry and other realtime applications. These transceivers 52A may use different hop sequences (in spread spectrum embodiments) or different frequency bands (in fixed frequency embodiments) to prevent interference with one another. As described below, access point transceivers 52A that are spaced apart by a sufficient distance to avoid interference may use the same hop sets or frequency bands to provide efficient utilization of the available bandwidth.

The use of sockets 50, 52 which receive removable transceiver or locator modules 50A, 50B allows each access point 30 to be configured as desired within a particular installation. Further, the design allows the access point to be easily updated over time to accommodate additional or different frequency ranges and device interfaces.

As depicted in FIG. 3, the access point 30 also includes the following components, all of which are interconnected by a bus: a processor 54, respective controllers 56, 58 for controlling the transceiver modules 50A, 52A, RAM and FLASH memory 60, 62, and a network interface 66 such as 100 BaseT. These and the other various components of the access point may be combined within a common housing that is adapted to be mounted to the ceiling or a wall within the medical facility. The access points may be powered over the network interface (e.g., using the power-over-Ethernet standard being developed by the IEEE802.3af committee) or by a separate DC power supply.

The processor 54 may runs a realtime operating system such as pSOS, although a non-realtime operating system may alternatively be used. The processor also runs Ethernet agent software capable of supporting a variety of off-the-shelf PCMCIA form factor 802.11 modules 50A. The agent software allows for the simultaneous operation of all supported device interfaces. The access point may also include an RS-422 or other receiver 64 that may be used for synchronizing the access points.

As shown in dashed lines, the access point 30 may also include a second network interface 66' for connecting to a second LAN (as mentioned above). The second network interface may be used in systems in which separate LANs are used for time-critical versus non-time-critical applications (as in FIG. 2). In these configurations, the gateway software links the WMTS transceivers 34 with the LAN 32A used for time-critical applications, and interconnects the 802.11 or other non-realtime transceivers 36 with the LAN 32B used for non-realtime applications. The location tracking modules 49A may be linked to either or both LANs 32A, 32B.

Figure 4:
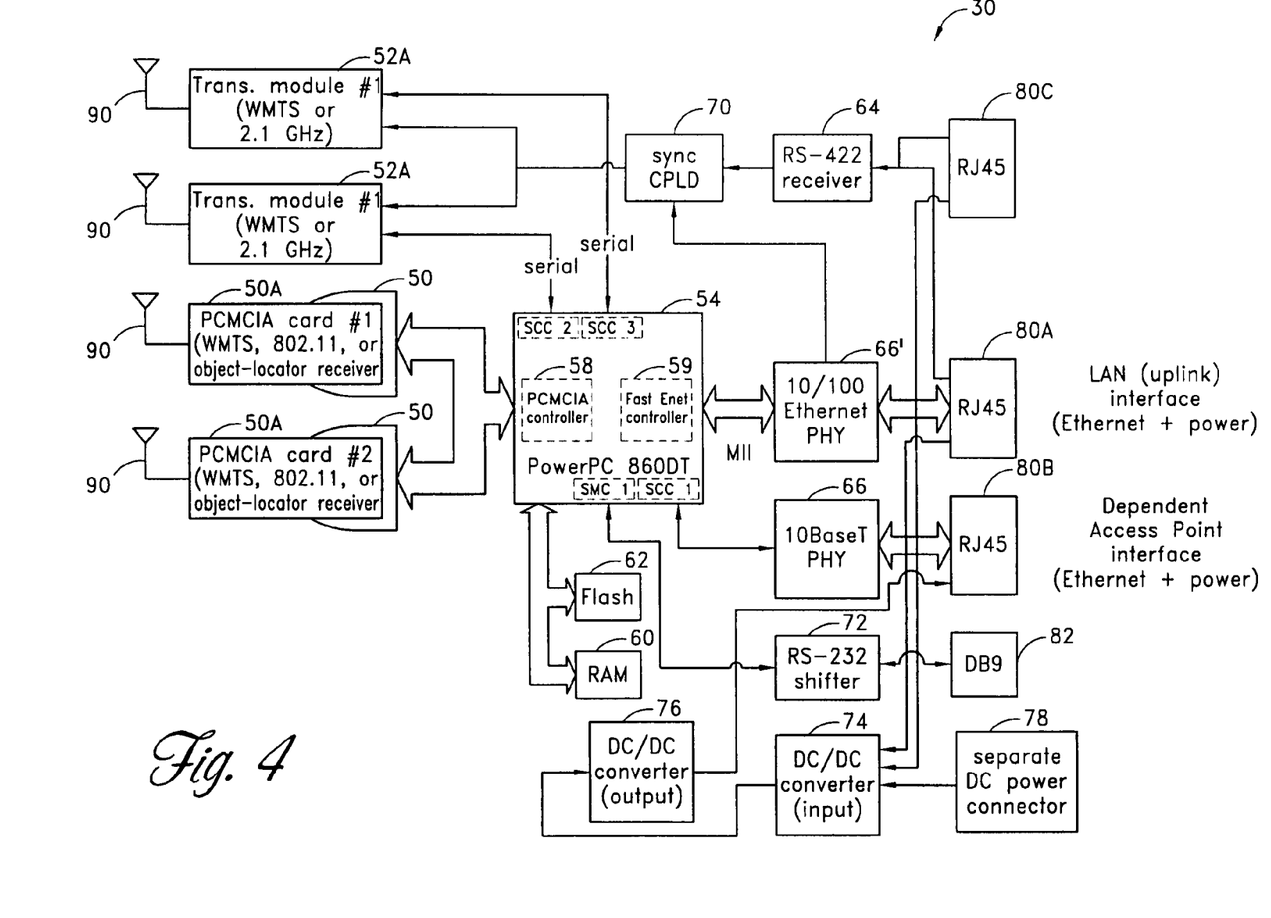
FIG. 4 illustrates an example implementation of the architecture of FIG. 3.

FIG. 4 illustrates an example implementation of the access point depicted in 30 FIG. 3. In this embodiment, the processor 54 is a Motorola MPC86ODT, which includes a PCMCIA controller 58, a fast Ethernet controller 59, serial communication controllers (SCC1–SCC3), and a serial management controller (SMC1). In addition to the components discussed above, the access point system includes a sync CPLD (complex programmable logic device) 70, a 10/100 Ethernet PHY (physical layer interface) 66, a 10BaseT physical layer interface 66', an RS-232 shifter 72, DC-to-DC converters 74, 76, a DC power connector, three RJ45 connectors 80A–80C, and a D-subminiature 9-pin connector (DB9) 82.

The sync CPLD 70, RS-422 receiver 64, and uppermost RS45 80C jack are used to send and receive sync pulses for maintaining the access points 30 in synchronization. Any of a variety of alternative synchronization methods may be used. The lowermost RJ45 connector 80B may be used either to connect the access point to a second LAN, or to connect the access point to second, dependent access point.

Although each RF module 50A, 52A is illustrated with its own respective antenna 90, one or more antennas may be shared by the RF modules 50, 52. Further, a given transceiver module may be coupled to multiple antennas 90 in order to implement a spatial diversity scheme. Other forms of diversity, including time, frequency and angle diversity, may additionally or alternatively be used. The circuitry for implementing the particular diversity scheme or schemes may be embedded within the transceiver modules 50A, 52A. An example of a specific antenna design that may be used with the access points 30 is described below under the heading "antenna design."

III. Flow Control to Limit Latency for Time-Critical Data

Where a single hardwired LAN 32 is used to carry both time-critical and non-time-critical data transmissions, a flow control mechanism may be used to essentially guarantee that the time-critical transmissions satisfy predefined latency requirements. By way of background, in the design set forth above, the time-critical data are characterized by a bounded total data rate which is a small fraction of the total available data throughput of the LAN 32 at any particular time. For example, a single WMTS access point 30B typically will not source more than 1 megabit/second (Mbps) of realtime data, compared to a high speed IEEE 802.11b access point which might source/sink up to 3–4 Mbps. The access point's 100BaseT interface 66, on the other hand, is capable of sourcing or sinking in excess of 30 Mbps. Thus, flow control of the non-realtime traffic is generally needed only in response to upstream congestion-flow control actions (i.e. further up the hardwired network 32 toward the eventual sinks of the non-time-critical data).

Where such congestion conditions exist, any of a variety of standard flow control mechanisms may be used to restrict the flow of non-realtime traffic. Examples of such flow control mechanisms for Ethernet include false carrier sense for half duplex links and IEEE 802.3X PAUSE packets for full duplex links. The multi-band access point may respond to these mechanisms by throttling the non-realtime (802.11) data source onto the LAN. For example, if an 802.11 access point were connected to the multi-band access point via a separate secondary Ethernet segment (the "dependent access point" interface in FIG. 4), then the main access point can buffer packets from the 802.11 access point in its local memory while asserting the flow control condition on the secondary Ethernet interface.

Typically, the primary data flow directions are opposite between the two traffic types. Specifically, most of the WMTS data flows from the wireless remote devices 34 onto the hardwired network 32 (mostly processed physiological data, e.g. ECG waveforms), with only a relatively small data flow from the hardwired LAN to the wireless remotes (mostly control data); in contrast, most of the 802.11 or other standard WLAN traffic (typically data served from LAN servers 40, 42, 46, 48) flows from the hardwired network 32 to the wireless devices 36 (PDAs, etc.). Because full-duplex network hardware is used to implement the hardwired network 32, these two primary flows do not compete with each other.

IV. Wireless Access Points

The access point design set forth above may also be used to provide wireless access points that are not physically connected to hardwired hospital network 32.

Wireless network access points may be used to provide data reception coverage where it would be difficult or expensive to run the hardwired LAN to the access point. For example, a wireless access point could be attached to a streetlight within a hospital parking lot; such an access point could be used to monitor patients both inside and outside the building since the RF energy passes through the windows.

To monitor patients with a wireless access point, one or more WMTS transceiver modules 50A, 52A may be used to communicate with the patient transceiver 34, while another one or more transceiver modules 50A, 52A (WMTS or 802.11) of the same wireless access point is used to relay the realtime patient data to a hardwired access point. A point-to-point link may be established between the wireless and hardwired access points 30 for this purpose using directional antennas. The wireless access points may also be used to support non-time-critical channels and applications.

V. Frequency Reuse and Timeslot Dithering

In some cases, the total data throughput (for the complete system) required for time-critical applications may exceed the available RF spectrum. To overcome this problem, access points 30 that are spaced sufficiently apart from one another may be assigned to the same channel, as described in the '659 patent, so that frequencies are reused in different regions of the medical facility. For example, two access points 30 may be assigned to the same frequency channel (in fixed frequency implementations) or to the same hop set (in frequency hopping implementations). In one preferred embodiment, WMTS frequencies are reused by allowing access points to share the same hop set.

Where frequencies are reused, two wireless devices 34 (e.g., patient transceivers) within the medical facility may transmit a packet on the same frequency at the same time. Normally, such coincident transmissions do not interfere with one another because the access points 30 (and thus the wireless devices) are sufficiently spaced apart. In some circumstances, however, the coincident transmissions may nevertheless interfere with each other such that an access point 30 fails to receive the transmitted data (referred to herein as a "collision"). A collision may occur, for example, when an air conditioning duct acts as a waveguide with respect to the transmission frequency, causing the signal generated by a wireless device 34 to propagate to distance access points 30 (referred to as "anomalous propagation"). In such circumstances, it may not be possible, for example, to monitor one or both patients for an extended period of time typically until the patient that is the source of the interference moves away from the structure causing the propagation anomaly.

To reduce or avoid such lockstep interference, the system may use an inventive 30 timeslot assignment or "dithering" method in which the WMTS transmitters (patient transceivers) 34 connected to a particular access point 30 rotate or otherwise vary their transmission timeslots over time according to a sequence or pattern that is known to the access point 30. For example, all WMTS transmitters connected to access point #1 may rotate their timeslot assignments by one slot position per frame, while all WMTS transmitters connected to access point #2 may rotate their timeslot assignments by two slot positions per frame. The sequences or patterns used to vary the timeslot assignments are selected such that if any given pair of devices produce coincident transmissions (transmissions that occur at the same time on the same frequency) during a particular frame, that pair will not again produce coincident transmissions for a large number of consecutive frames (e.g., 100 or 1000 frames). Thus, collisions between a given pair of transmitters do not occur in lock step, and will occur, at most, on an infrequent basis.

Table I depicts a simple example for purposes of illustrating the basic concept of time slot dithering. In this example, it is assumed that the access points 30 operate on fixed frequencies (no hopping) using a TDMA frame that includes four timeslots (0–3), and that each transmitter transmits during exactly one timeslot per frame. The letter A represents a transmitter 34 that is connected to an access point in which timeslots are rotated forward by three slots every frame. The letter B represents a transmitter 34 connected to an access point for which timeslots are rotated forward by two timeslots on every third frame. It is further assumed that the two access points operate (receive data) on the same, fixed frequency. As depicted in FIG. 1, transmitters A and B produce coincident (potentially colliding) transmissions during one out of every eight frames (frames 1 and 9 in the illustrated example). Thus, as most, one eighth of the transmissions by transmitter A will be lost due to transmissions from transmitter B, and vice versa. The same holds true for any other pair of transmitters that use the same access points. In practice, the frames include a larger number of slots (e.g., 10 slots), permitting a significantly greater separation in time between coincident transmission by any given pair of transmitters.

TABLE I

| Frame | Slot 0 | Slot 1 | Slot 2 | Slot 3 |
|-------|--------|--------|--------|--------|
| 1 | A, B | | | |
| 2 | B | | | A |
| 3 | B | | A | |
| 4 | | A | B | |
| 5 | A | | B | |
| 6 | | | B | A |
| 7 | B | | A | |
| 8 | B | A | | |
| 9 | A, B | | B | |
| | | | B | A |

In practice, ducting and other causes of anomalous propagation are frequency selective. Thus, collisions tend to occur, if at all, only on a small subset of the WMTS frequencies used by the system. In systems that use frequency hopping, potentially colliding transmissions can therefore be further reduced by coordinating the slot assignment scheme with the frequency hopping scheme—i.e., by simultaneously hopping both the timeslot and the channel (frequency). In a preferred embodiment, this is accomplished by using timeslot and frequency channel hopping patterns that are pseudo-random with low cross-correlation, so that the interval between hops where a given transmitter is potentially jammed can be made as long as the product of the periods of the two pseudo-random sequences. With this approach, if a given transmitter 34 is victimized by anomalous propagation (i.e., if another transmitter on the same hopset-timeslot pair causes that particular timeslot to be jammed), then on the next hop the transmitter causing the anomalous propagation will (at worst) jam a different transmitter 34. Since a well designed frequency hopper allows throughput margin for the failure of occasional individual hops, the timeslot hopping in essence distributes the loss of spectrum associated with the anomalous propagator in such a way that there is no actual performance loss for any transmitter 34.

Timeslot dithering is used in the preferred embodiment for communications within the WMTS band, but may be employed within other frequency bands, including those used for non-time-critical applications.

VI. Antenna Design

Another inventive feature of the system is an access point antenna that provides highly optimal price/performance within hospital wireless LANs. The antenna is preferably used solely for WMTS communications (using a separate off-the-shelf antenna for the ISM band), but could be used for both WMTS and ISM bands.

Figure 5:
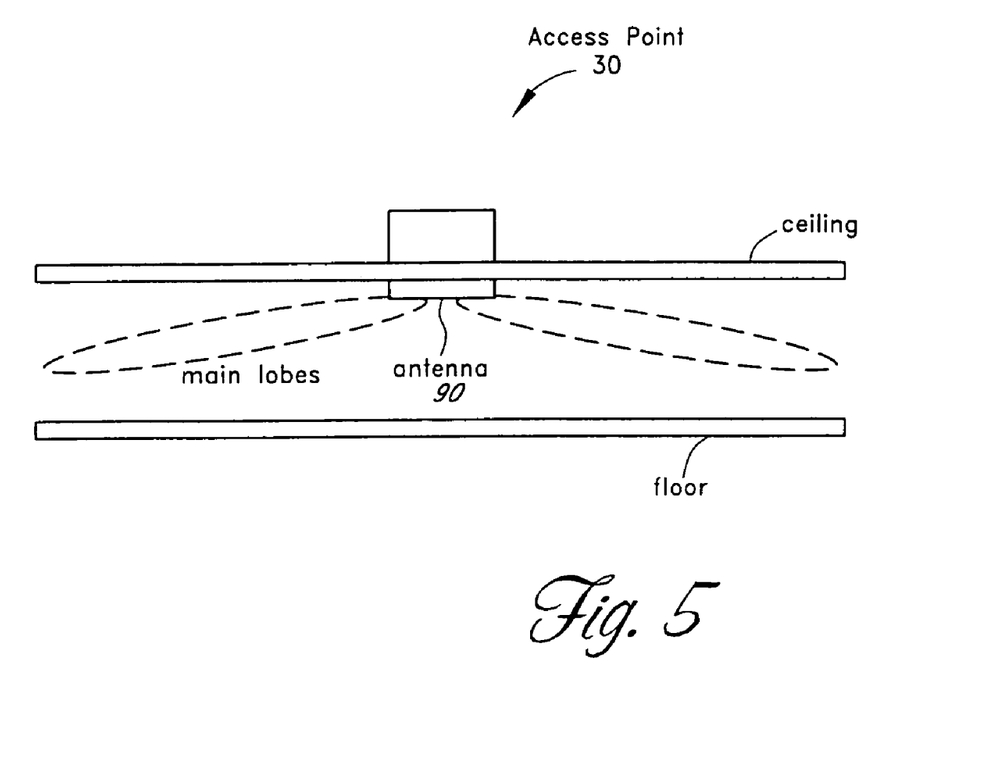
FIG. 5 illustrates how the access points may be mounted to a ceiling.

As depicted generally in FIG. 5, the antenna 70 is adapted to be mounted to the 10 ceiling, which is typically a drop ceiling. In the illustrated embodiment, the access point electronics and associated housing are positioned above the ceiling panel, and are connected to the antenna and its associated housing 90 by a conductor that extends through the ceiling panel. In another embodiment (not illustrated), the access point electronics and antenna are integrated within a common housing. The use of a common housing for this purpose reduces the overall size of the access point 30 while reducing installation costs.

In accordance with the invention, the antenna design is characterized by the combination of four primary features. The first feature is a narrow, bi-lobed pattern in elevation, with maximum gain at about 5° to 10° above horizon. Since the antenna hangs from the ceiling in an upside down orientation, this design attribute results in the lobes pointing away from the antenna's center and slightly toward the floor (as shown in FIG. 5). This orientation focuses most of the antenna's energy in the direction where maximum range is needed, and provides some rejection against interference sources.

The second feature involves the use of either an omni-directional or a bi-lobed 25 (peanut shaped) azimuth pattern. The bi-lobed pattern is best for long hallways with single rows of patient rooms on either side of the hallway, which is a very common construction pattern for hospitals. The omni-directional azimuth pattern is best when there is not a major axis to the floor plan.

The third feature involves the use of elliptical polarization. As is well known in 30 the art, elliptical polarization is similar to circular polarization but has a strongly preferred axis (3 dB to 6 dB higher in gain than the weaker axis). The antenna is preferably mounted with the predominant axis roughly vertical and with the weaker access roughly horizontal. This orientation is well suited for picking up weak, reflected signals from patient transceivers that do not have a direct transmission path to the access point. Specifically, the vertical axis is responsive to vertically polarized energy reflected from vertical scattering surfaces (e.g. mirrors, and the aluminum studs in drywall constructions), while the horizontal axis enables reception of horizontally polarized energy reflected from horizontal scattering surfaces (e.g., metal trays and carts, heating/air conditioning ducts in the ceiling, pipes, etc.). The existence of the predominant vertical axis is desirable because vertical scattering surfaces tend to be more common within hospitals than horizontal scattering surfaces.

The fourth feature is polarization diversity. By way of background, the traditional approach to antenna diversity in medical telemetry has been space diversity, which typically involves two antennas separated (ideally) by an odd number of quarter wavelengths. Space diversity has two problems: (A) it requires two physical antennas, increasing the cost and physical intrusiveness of the installation, and (B) for any possible arrangement of two antennas, there are angles of incidence from which both antennas can simultaneously be at nulls from the transmitter.

The polarization diversity antenna contains two at least partially orthogonal polarizations. In the simplest case, the two polarizations are vertical and horizontal. More preferably, the polarizations are elliptical with a 30–40 degree angle between their major axes. With this arrangement, for any linearly polarized energy at least one axis will respond (avoiding the equivalent of problem B above). The polarization diversity antenna can be implemented with two interleaved arrays of radiating elements on the same substrate, so the cost increase is only a small factor (40%) rather than a factor of two (avoiding problem A above).

The features set forth above may be incorporated into an antenna design using techniques that are well known in the art. Table II below summarizes the specifications of one particular implementation of the above-described antenna design.

TABLE II

ANTENNA SPECS

| | |
|---|---|
| FREQUENCY: | 608–614 MHz |
| POLARIZATION: | Elliptical, i.e. major axis 3 dB to 6 dB greater than minor axis |
| GAIN: | Measured with respect to vertical linear polarization. +2 dBi or greater at elevation +5°, all azimuths. +0 dBi or greater at all elevations between +2° and +150, all azimuths |
| DIVERSITY: | Polarization diversity, major axis of first diversity leg −30° to −20° off vertical, major axis of second diversity leg +20° to +30° off vertical |

VII. Example Applications

In addition to the patient monitoring, patient location tracking, and other functions set forth above, the system may be used to support a variety of other types of applications. Several examples of such applications are described below, each of which may be implemented through application software running on the hardwired network 32 combined with appropriate wireless devices using methods that are known in the art.

Staff/employee location. Hospital employees may be provided with badges or other devices that contain small, battery-powered location tracking devices 36D. Application software running on the network 32A may use these devices to keep track employee locations. The employee location data may, for example, be incorporated into a clinician paging or dispatching system to help identify the clinician best suited to handle a patient call or an emergency.

Equipment Tracking. As mentioned above, location tracking devices 36D may also be attached to or incorporated within various types of hospital equipment, including (for example) portable X-ray machines, portable defibrillators, bedside monitors, wheelchairs, portable beds, laptop computers, and PDAS. A desktop application may be used to locate such equipment by type, region (e.g., floor), ID number, or other criteria.

Patient Flow Analysis. The patient location data stored by the location tracking server 48 may be used for various forms of patient flow analysis. For example, the data may be used to track the occupancy of each patient unit within the medical facility. A patient flow modeling program in turn use the occupancy data to predict unit overflow conditions and flow bottlenecks, so that administrators can take preventative measures (e.g., move extra beds to a step down ward) before such problems occur. Patient flow monitoring may also be used by medical facilities to evaluate the desirability of purchasing new equipment. Examples of computer-implemented methods for modeling patient flow are described in U.S. Provisional Appl. No. 60/192,806, filed Mar. 29, 2000, the disclosure of which is hereby incorporated by reference.

Inventory of Disposable Equipment. The object location tracking features of the system may also be used to maintain an inventory of disposable equipment such as catheters and implantable devices. In one embodiment, a special location tracking device 36D is used which automatically deactivates itself (discontinues transmissions) when detached from the disposable item. The location tracking device may alternatively be designed to transmit a special signal upon detachment. When a clinician detaches the location tracking device from the disposable item, a software application running on the network detects the detachment event and updates an inventory database accordingly.

Point of Care Data Entry and Retrieval. Clinicians may be provided with 802.11 writing tablets 36C or other data input devices 36 for entry of patient data into a database. The writing tablets and/or other devices may also permit the clinician to 25 retrieve patient data from the database. The devices 36 may be provided with bar code scanners or other types of patient ID readers to allow the clinician to efficiently identify the patient to the system.

Pharmacy/Prescriptions. The system may also implement a prescription system in which doctors use the writing tablets 36C or other devices 36 to scan-in patient bar codes and enter prescriptions at the patient's bedside. The prescription would be sent via the 802.11 WLAN and hospital network 32 to a pharmacy database for fulfillment, and may automatically be checked for drug interaction problems. Once the pharmacy delivers the prescription to the patient unit, a nurse may scan-in the bar code on the prescription container for comparison with that of the patient. In addition, the nurse may scan-in the patient and prescription bar codes for entry into the patient's electronic chart each time the drug is administered.

Paging. The system may implement a two-way paging system, which may be integrated with the realtime patient monitoring system. In one embodiment, for example, when the realtime patient monitoring system detects an alert condition (e.g., an arrhythmia), a human dispatcher is notified and is prompted to page a clinician. Upon receiving the message on an 802.11 or other paging device, the clinician is prompted to acknowledge the page, and is presented an option to view the physiologic data (such as an ECG snapshot) that gave rise to the alert condition; this data may be retrieved from the physiologic data server 46. The clinician may also have the option to retrieve patient data from a CIS server or another system on the hardwired network 32. If the clinician fails to respond to the page within a predefined timeout period, the dispatcher may be prompted to page a different clinician. An audit trail of the alert conditions, paging events, and clinician acknowledgements may be stored by the paging system for subsequent viewing.

The system may also be used for the following: remote offsite maintenance of transceivers and equipment; voice and video communication (including video conferencing); communication of digital photos of clinically relevant items; communication of radiological and Sonographic data (e.g., to remote medical facilities or to physician's homes); electronic retrieval of patient's chart at the bedside, and communication of EEG and sleep study data (both within the hospital facility and remote monitoring from the homes).

Although this invention has been disclosed in the context of certain preferred 30embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. An access point used to track a location of a plurality of patients in a medical facility, comprising:
   a first transceiver module which implements a realtime wireless protocol to transfer time-critical wireless data to the hardwired network with a known maximum latency; and
   a second transceiver module which implements a non-realtime wireless protocol to provide non-realtime wireless access to the hardwired network, wherein the access point communicates via the first transceiver module and the second transceiver module simultaneously, and further wherein the first transceiver module is used to track the location of the plurality of patients.

2. The access point of claim 1, further comprising a wireless patient transceiver which transmits realtime patient data to the first transceiver module.

3. The access point as in claim 1, wherein the realtime WLAN protocol is a TDMA protocol.

4. The access paint as in claim 3, wherein the non-realtime WLAN protocol is an 802.11 WLAN protocol.

5. The access point as in claim 1, wherein the non-realtime WLAN protocol is an 802.11 WLAN protocol.

6. The access point as in claim 1, wherein the non-realtime WLAN protocol is a link management protocol (LMP).

7. The access point as in claim 1, wherein the first transceiver module operates in a WMTS band, and the second transceiver operates in an ISM band.

* * * * *